(12) United States Patent
Hlavka et al.

(10) Patent No.: US 10,555,746 B2
(45) Date of Patent: Feb. 11, 2020

(54) DEVICES AND METHODS FOR TREATING CONDITIONS CAUSED BY AFFARENT NERVE SIGNALS

(71) Applicant: HOLOGIC, INC., Marlborough, MA (US)

(72) Inventors: Edwin J. Hlavka, Minneapolis, MN (US); Eric Whitbrook, Maple Grove, MN (US); Peter T. Keith, Lanesboro, MN (US); Thomas V. Ressemann, Maple Grove, MN (US)

(73) Assignee: HOLOGIC, INC., Marlborough, MA (US)

( * ) Notice: Subject to any disclaimer, the term of this patent is extended or adjusted under 35 U.S.C. 154(b) by 463 days.

(21) Appl. No.: 14/614,303

(22) Filed: Feb. 4, 2015

(65) Prior Publication Data

US 2015/0216532 A1 Aug. 6, 2015

Related U.S. Application Data

(60) Provisional application No. 61/935,753, filed on Feb. 4, 2014.

(51) Int. Cl.
*A61B 17/12* (2006.01)
*A61B 17/00* (2006.01)
*A61B 17/32* (2006.01)
*A61B 1/307* (2006.01)
*A61B 1/00* (2006.01)

(52) U.S. Cl.
CPC .. *A61B 17/320016* (2013.01); *A61B 1/00087* (2013.01); *A61B 1/307* (2013.01)

(58) Field of Classification Search
CPC ......... A61B 2017/00805; A61B 2017/320048; A61B 2017/320076; A61B 17/320016
See application file for complete search history.

(56) References Cited

U.S. PATENT DOCUMENTS

| | | | |
|---|---|---|---|
| 5,342,353 | A | 8/1994 | Allen |
| 5,370,675 | A | 12/1994 | Edwards |
| 5,378,675 | A | 1/1995 | Takeyama et al. |
| 5,667,488 | A | 9/1997 | Lundquist et al. |
| 5,672,153 | A | 9/1997 | Lax et al. |
| 5,964,727 | A | 10/1999 | Edwards et al. |
| 6,129,726 | A | 10/2000 | Edwards et al. |
| 6,190,353 | B1 | 2/2001 | Makower et al. |

(Continued)

FOREIGN PATENT DOCUMENTS

| | | |
|---|---|---|
| AU | 2010319333 B2 | 2/2014 |
| CN | 103764225 A | 4/2014 |

(Continued)

OTHER PUBLICATIONS

WIPO International Searching Authority, International Search Report and Written Opinion dated Jun. 24, 2015 in International Patent Application No. PCT/US2015/014500, 11 pages.

(Continued)

*Primary Examiner* — Anh T Dang
(74) *Attorney, Agent, or Firm* — Vista IP Law Group LLP

(57) ABSTRACT

Devices and methods for treating conditions, such as overactive bladder, caused by afferent nerve signals involving the creation of dissection planes that interrupt the afferent nerve signals.

18 Claims, 16 Drawing Sheets

(56) References Cited

U.S. PATENT DOCUMENTS

| | | |
|---|---|---|
| 6,216,704 B1 | 4/2001 | Ingle et al. |
| 6,231,518 B1 | 5/2001 | Grabek et al. |
| 6,325,798 B1 | 12/2001 | Edwards et al. |
| 6,419,653 B2 | 7/2002 | Edwards et al. |
| 6,425,877 B1 | 7/2002 | Edwards |
| 6,610,054 B1 | 8/2003 | Edwards et al. |
| 6,626,930 B1 | 9/2003 | Allen et al. |
| 6,632,193 B1 | 10/2003 | Davison et al. |
| 6,692,490 B1 | 2/2004 | Edwards |
| 6,852,091 B2 | 2/2005 | Edwards et al. |
| 6,960,205 B2 | 11/2005 | Jahns et al. |
| 7,818,039 B2 | 10/2010 | Jahns et al. |
| 8,641,711 B2 | 2/2014 | Kelly et al. |
| 8,657,814 B2 | 2/2014 | Werneth et al. |
| 8,684,998 B2 | 4/2014 | Demarais et al. |
| 8,721,632 B2 | 5/2014 | Hoey et al. |
| 8,740,896 B2 | 6/2014 | Zarins et al. |
| 8,758,337 B2 | 6/2014 | Skwarek et al. |
| 8,771,267 B2 | 7/2014 | Kunis et al. |
| 8,771,269 B2 | 7/2014 | Sherman et al. |
| 8,790,281 B2 | 7/2014 | Diederich et al. |
| 8,840,625 B2 | 9/2014 | Adams et al. |
| 2002/0002372 A1 | 1/2002 | Jahns et al. |
| 2002/0193851 A1 | 12/2002 | Silverman |
| 2003/0032860 A1 | 2/2003 | Avni et al. |
| 2004/0059389 A1 | 3/2004 | Chornenky |
| 2004/0186468 A1 | 9/2004 | Edwards |
| 2004/0215179 A1 | 10/2004 | Swoyer et al. |
| 2007/0112340 A1 | 5/2007 | Thomas et al. |
| 2009/0069803 A1 | 3/2009 | Starkebaum |
| 2009/0171315 A1 | 7/2009 | Versi |
| 2010/0174306 A1 | 7/2010 | Mitelberg et al. |
| 2010/0256446 A1 | 10/2010 | Raju |
| 2011/0112434 A1 | 5/2011 | Ghabrial et al. |
| 2012/0048417 A1 | 3/2012 | Smith |
| 2012/0048419 A1 | 3/2012 | Giribona |
| 2012/0123411 A1 | 5/2012 | Ibrahim et al. |
| 2013/0018281 A1 | 1/2013 | Nagale |
| 2013/0030249 A1 | 1/2013 | Vazales et al. |
| 2013/0066308 A1 | 3/2013 | Landman |
| 2013/0072855 A1 | 3/2013 | Sherry et al. |
| 2013/0090640 A1 | 4/2013 | Nagale et al. |
| 2013/0090648 A1 | 4/2013 | Nagale et al. |
| 2013/0172864 A1 | 7/2013 | Ibrahim et al. |
| 2014/0012247 A1 | 1/2014 | Bakos et al. |
| 2014/0012256 A1 | 1/2014 | Deem et al. |
| 2014/0018786 A1 | 1/2014 | Van Wyk et al. |
| 2014/0025055 A1 | 1/2014 | Burnett et al. |
| 2014/0031810 A1 | 1/2014 | Mahvi et al. |
| 2014/0039356 A1 | 2/2014 | Sachs et al. |
| 2014/0039491 A1 | 2/2014 | Bakos et al. |
| 2014/0081257 A1 | 3/2014 | Ghoniem |
| 2014/0148798 A1 | 5/2014 | Sachs et al. |
| 2014/0163548 A1 | 6/2014 | Christian |
| 2014/0200568 A1 | 7/2014 | Sharma |
| 2014/0207136 A1 | 7/2014 | De La Rama et al. |
| 2014/0257272 A1 | 9/2014 | Clark, III et al. |
| 2014/0276593 A1 | 9/2014 | Nagale et al. |
| 2014/0276726 A1 | 9/2014 | Model |
| 2016/0030107 A1 | 2/2016 | Herbst et al. |

FOREIGN PATENT DOCUMENTS

| | | | |
|---|---|---|---|
| CN | 102256560 B | 7/2014 | |
| CN | 104080418 A | 10/2014 | |
| EP | 2155093 B1 | 5/2011 | |
| EP | 2349045 B1 | 7/2014 | |
| EP | 2759276 A1 | 7/2014 | |
| EP | 2813192 A2 | 12/2014 | |
| WO | WO2013016588 A1 | 1/2013 | |
| WO | WO 2013016590 A1 * | 1/2013 | ......... A61B 18/1485 |
| WO | WO2013160772 A2 | 10/2013 | |
| WO | 2014004698 A1 | 1/2014 | |
| WO | 2014022379 A1 | 2/2014 | |
| WO | 2014022436 A1 | 2/2014 | |
| WO | 2014025394 A1 | 2/2014 | |
| WO | 2014026028 A1 | 2/2014 | |
| WO | 2014113724 A2 | 7/2014 | |

OTHER PUBLICATIONS

Chinese Patent Office, Office Action dated Jan. 4, 2016 in Chinese Patent Application No. 201280046659.X, 21 pages.

WIPO International Searching Authority, International Search Report and Written Opinion dated Nov. 26, 2012 in International Patent Application No. PCT/US2012/048419, 17 pages.

WIPO International Searching Authority, International Search Report and Written Opinion dated Nov. 21, 2012 in International Patent Application No. PCT/US2012/048417, 16 pages.

WIPO International Searching Authority, International Search Report and Written Opinion dated Aug. 25, 2015 in International Patent Application No. PCT/US2015/0032298, 10 pages.

* cited by examiner

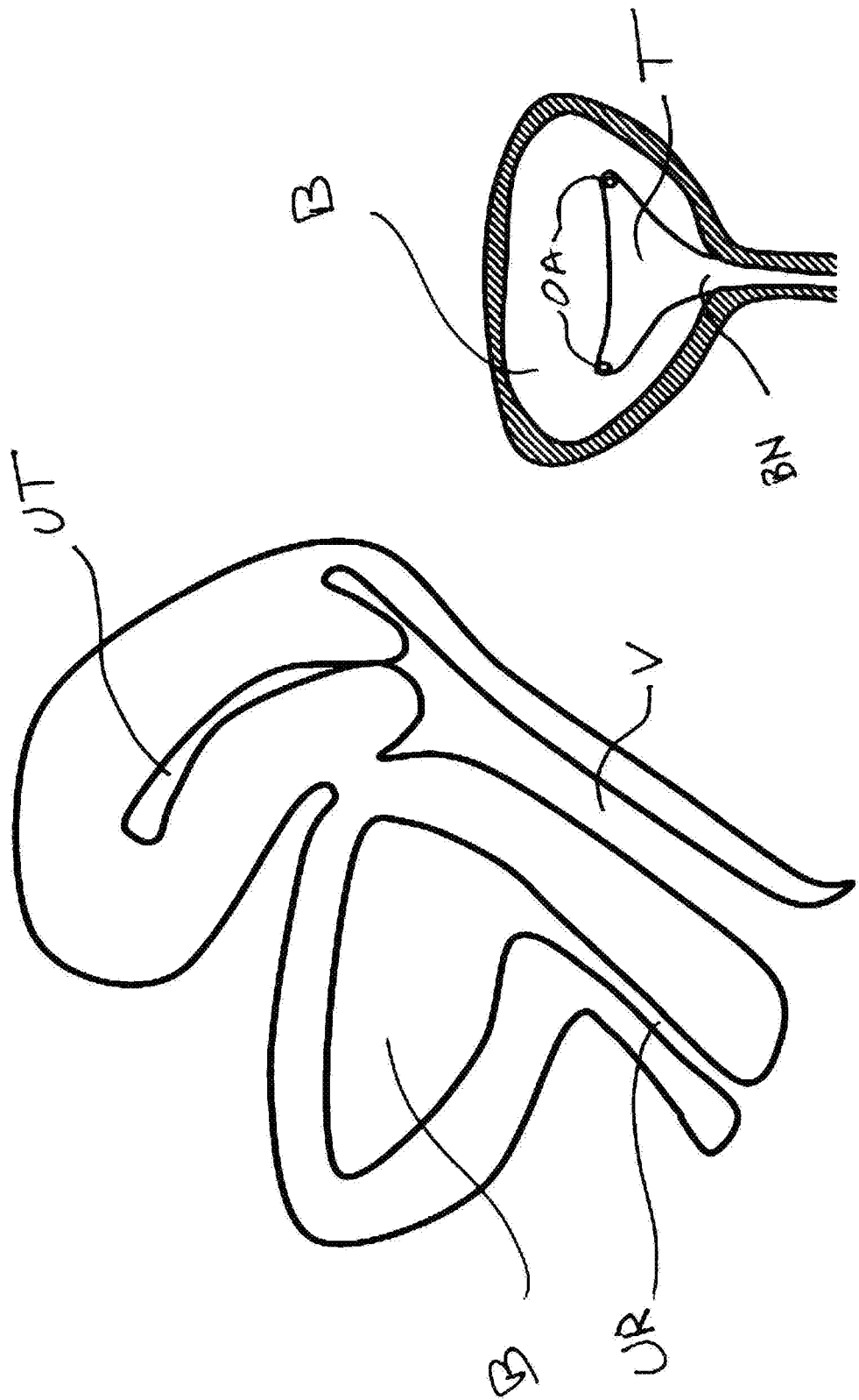

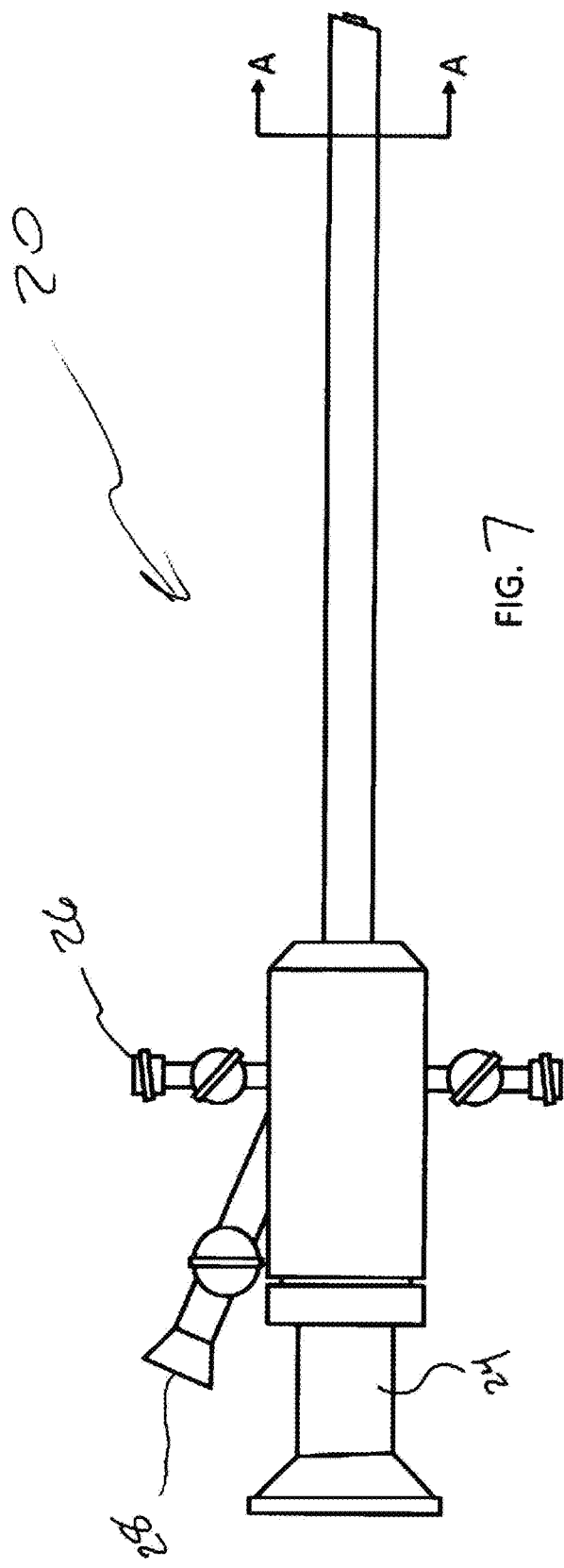
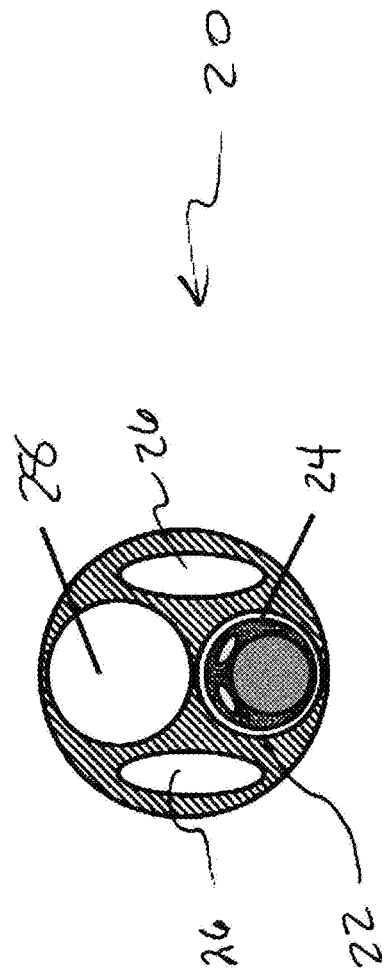
FIG. 7
FIG. 6

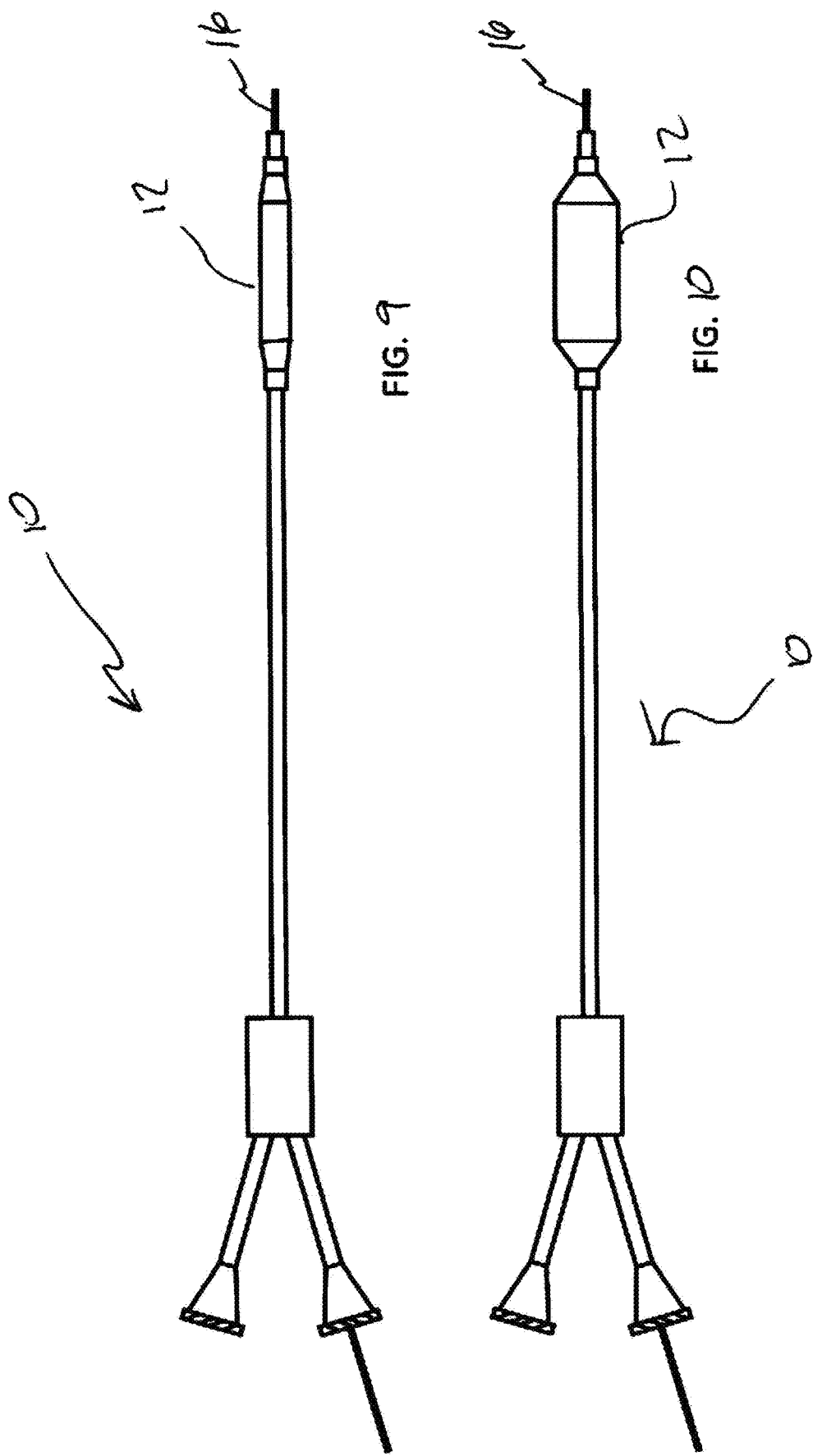

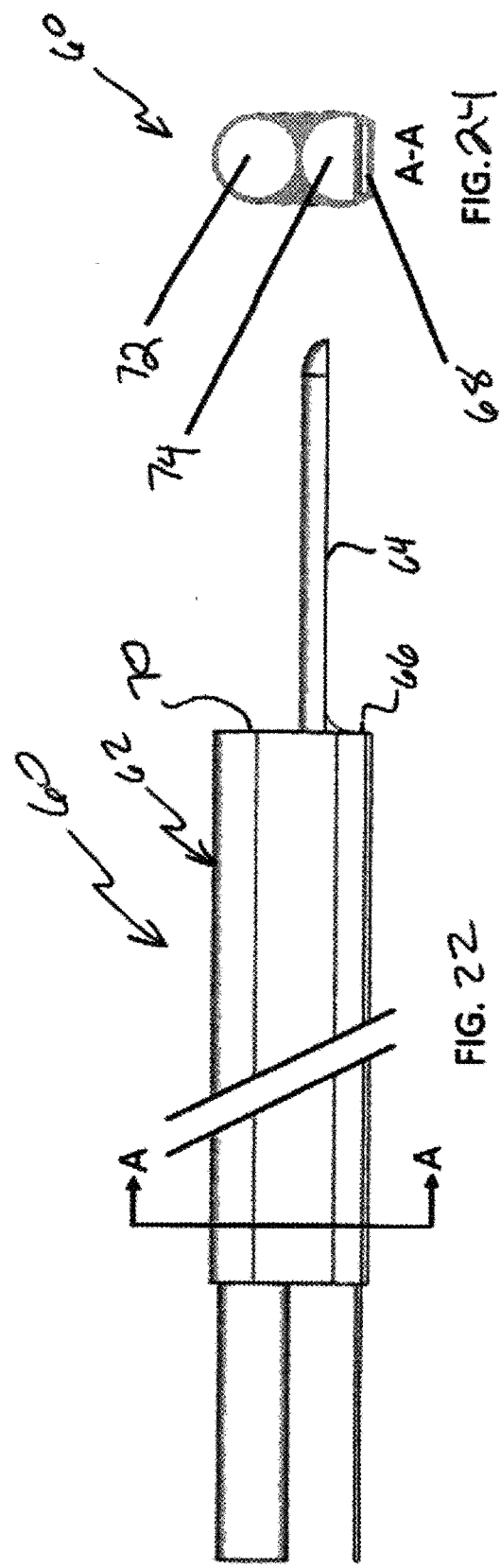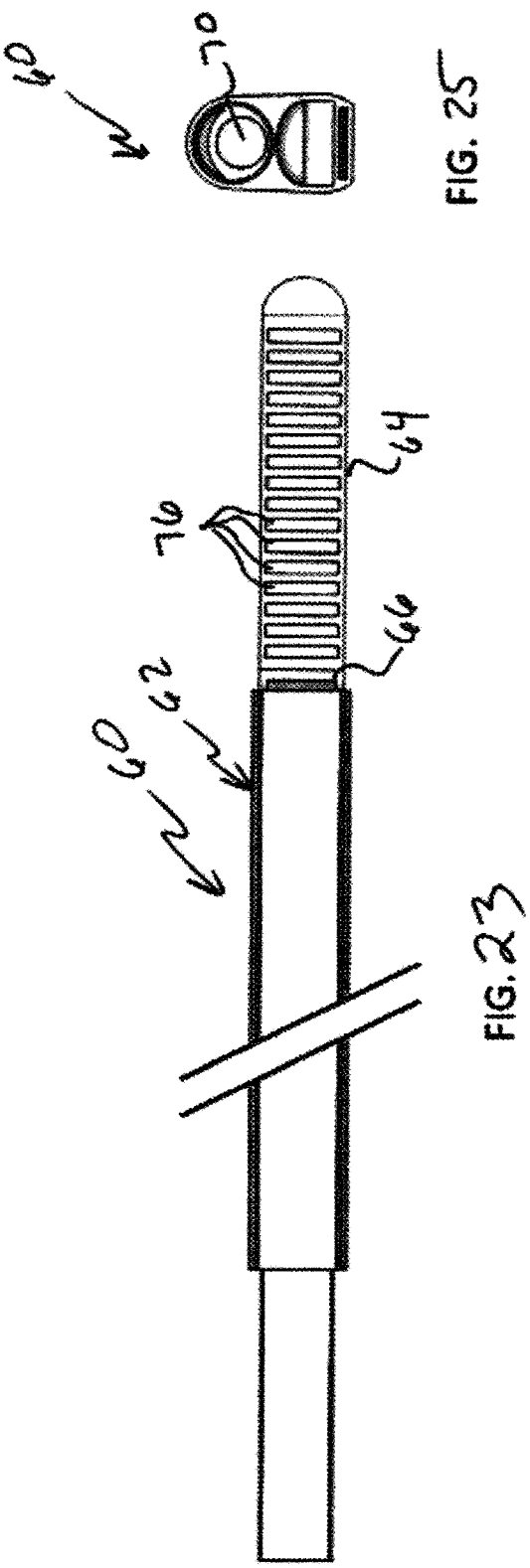

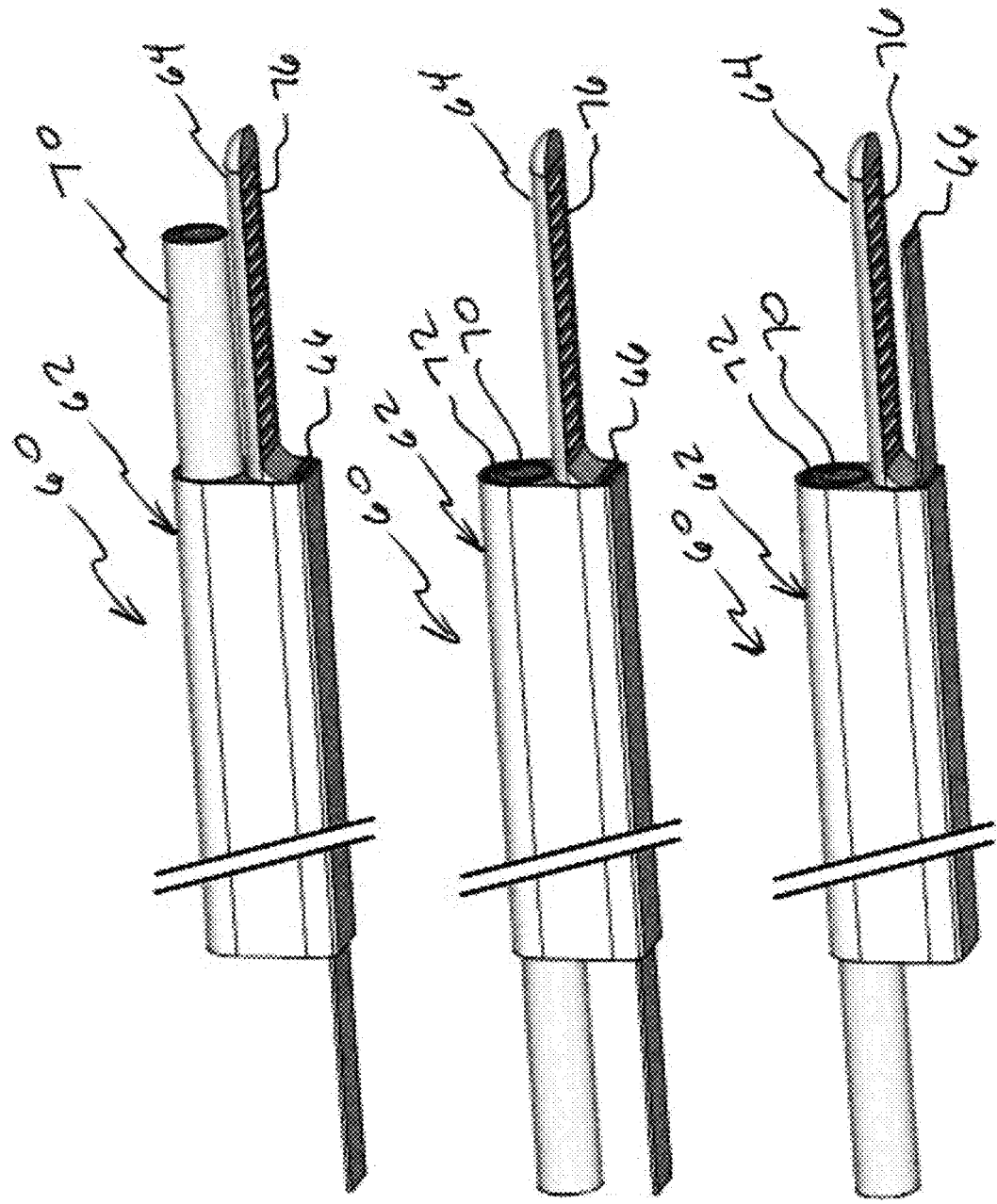

DEVICES AND METHODS FOR TREATING CONDITIONS CAUSED BY AFFARENT NERVE SIGNALS

RELATED APPLICATIONS

This application claims priority to U.S. Provisional Application Ser. No. 61/935,753 filed Feb. 4, 2014, entitled Devices And Methods For Treating Conditions Caused By Affarent Nerve Signals, which is hereby incorporated herein by reference in its entirety.

BACKGROUND OF THE INVENTION

The modified Inglemann-Sundberg (IS) procedure created a submucosal dissection plane in the trigone region of the bladder, for purposes of interrupting the afferent nerves emanating from the bladder trigone, as a treatment for OAB (Over active bladder). This dissection plane was created with basic surgical technique, via the superior portion of the vagina. A flap was created then re-approximated to result in a dissection layer within the congruent tissue of the vagina and trigone of the bladder. While apparently successful clinically, few physicians have adopted this. Even early study authors apparently do not continue to perform this procedure.

Some limiting factors in adoption of this procedure is its relative invasiveness, use of rudimentary surgical tools, together with the challenge of creating the dissection plane essentially blindly, without clear visual bladder landmarks from the vaginal approach.

OBJECTS AND SUMMARY OF THE INVENTION

Disclosed here are several concepts that mainly emulate the clinical result of the modified IS procedure, but do so in a way that would be more precise, less invasive, and/or easier to perform, as well as other potential advantages.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 is a diagram depicting the female urogenital anatomy;

FIG. 2 is a diagram of a female bladder;

FIG. 7 is an elevation of an embodiment of a visualization scope of the invention;

FIG. 8 is a section of the embodiment of FIG. 7 taken along section lines A-A;

FIGS. 9-10 are elevations of an embodiment of a catheter of the invention;

FIG. 22 is an elevation of an embodiment of a cutting device of the invention;

FIG. 23 is a bottom view of an embodiment of a cutting device of the invention;

FIG. 24 is an end view showing lumens of an embodiment of a cutting device of the invention;

FIG. 25 is an end view of an embodiment of a cutting device of the invention;

FIGS. 26-28 are perspective views of an embodiment of a cutting device of the invention; and, FIG. 29 is a perspective view of an embodiment of a cutting device of the invention.

DESCRIPTION OF EMBODIMENTS

Figure 3:
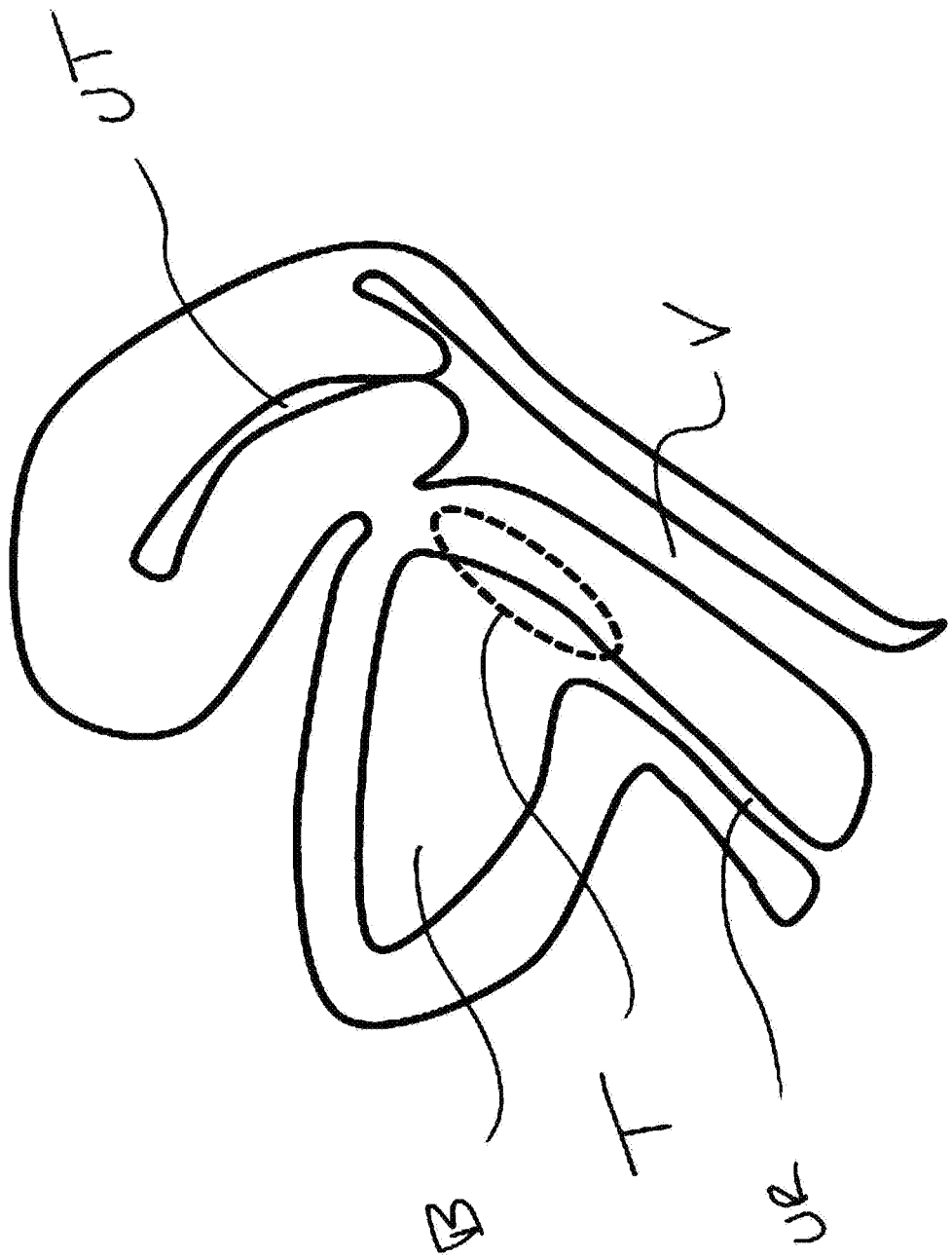
FIG. 3 is a diagram depicting the location of the trigone region of a female bladder in relation to the rest of the female urogenital anatomy.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 illustrates in sagittal section, the female urogenital organs. Bladder B, urethra UR, vagina V, and uterus UT. FIG. 2 shows the bladder B in frontal-axial section (parallel to urethra), illustrating the trigonal area or region T on the surface of the bladder, defined approximately by the triangle of the ureteral ostia UO, and bladder neck BN. The bladder anatomy of the male is similar.

Afferent nerves emanate from various locations within the bladder, but afferent nerves that emanate from the trigonal region T (dashed line in FIG. 3), are believed to play a particularly important role in modulating the urge to urinate. These afferent nerves travel from the bladder surface (mucosal layer) into the submucosal tissue and potentially into the vaginal layer coextant with the bladder trigonal tissue. Disruption of some or all of these nerves is believed to interfere with the pathological hyperactive voiding urge mechanism in people with over active bladder (OAB).

Figure 4:
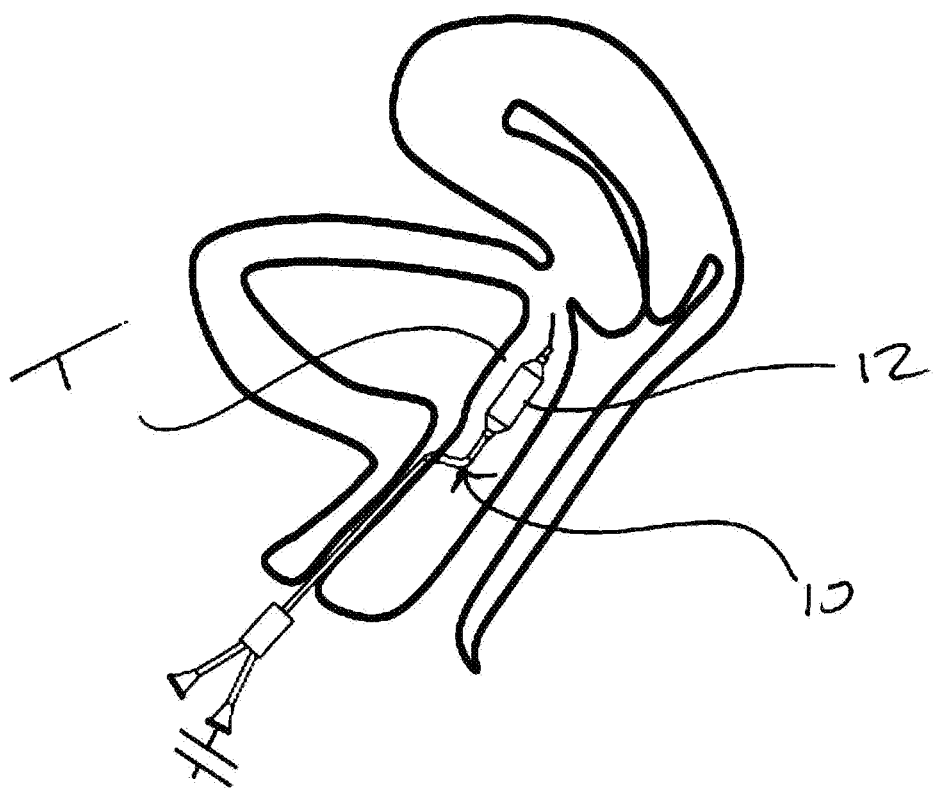
FIG. 4 is a diagram of an embodiment of a device of the invention being inserted into a female urogenital region.
Figure 6:
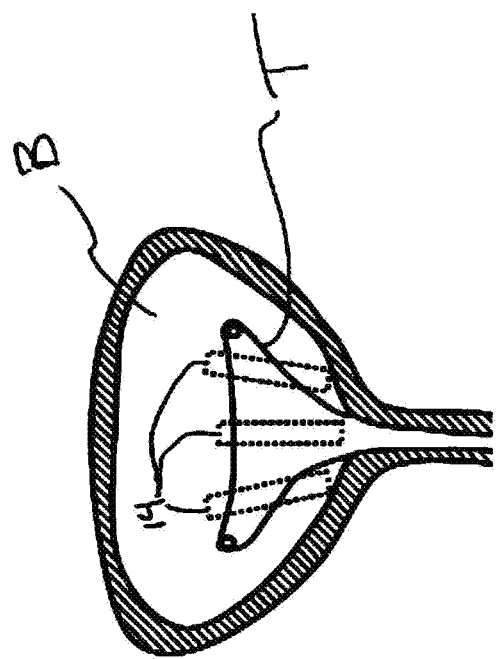
FIG. 6 is a diagram of multiple dissection layers formed by an embodiment of a method of the invention.

A first embodiment of a method of the invention shown in FIG. 4. Here, a balloon catheter 10 is placed in the submucosal tissue in the trigone region T. Upon inflation (using suitable inflation medium such as liquid or air), a dilated balloon 12 forms a dissection plane within the tissue, thus disrupting the afferent nerves therein. The balloon is then deflated and removed, resulting in the dissection layer 14 shown in FIG. 5. The balloon catheter 10 may be positioned in one or multiple locations. FIG. 6 shows the resultant dissected regions 14 of multiple placements and dilations. Multiple regions may be parallel, or "fanned out", as shown. The dissected regions or planes 14 may overlap, or be discontinuous (as shown). The size of the dissected plane(s) may be influenced by the balloon size, as well the number and position of the placements. The dissected plane(s) may be completely within the trigone region T, or may extend beyond the trigone region T. One or more dissected planes 14 may also be outside the trigone region T. The dissection plane(s) may be anywhere within the tissue of the bladder trigone, or in the vaginal wall. The plane(s) may be just under the mucosal layer, or at the junction of the vagina and bladder tissue. These layers may have a natural "separability" to facilitate relatively controlled dissectioning of the tissue.

The dissection plane(s) 14 may be stabilized following the dissecting procedure by temporary placement of a Fogarty balloon in the bladder to keep the dissected tissues in approximation. In this, as well as other embodiments of the invention, other suitable devices may also be used from either the bladder side and/or the vaginal side.

The dilation catheter 10 (which may also be an expandable mechanical dilator), may be placed with the aid of various devices, as described below. A representative visualization scope such as a cystoscope 20 is shown in FIGS. 7 and 8. This device 20 may include a channel 22 for an endoscope 24 (or could have built-in visualization), one or more channels 26 for infusion/aspiration, and one or more channels (lumens) for delivery of "working devices" (working channel) 28.

The dilation catheter 10, seen in FIG. 9 (uninflated balloon 12) and 10 (inflated balloon 12) may include a lumen for use with a guide wire 16. The guide wire lumen may extend the entire length of the balloon catheter, as is shown in the figures, or may emerge alongside, some distance from the tip, as is often the case with balloon catheters used in vascular procedures (aka "monorail style"). This shorter wire lumen allows for easier installation of the balloon catheter over the proximal end of the guide wire after the guide wire has been placed at a desired target location.

Figure 11:
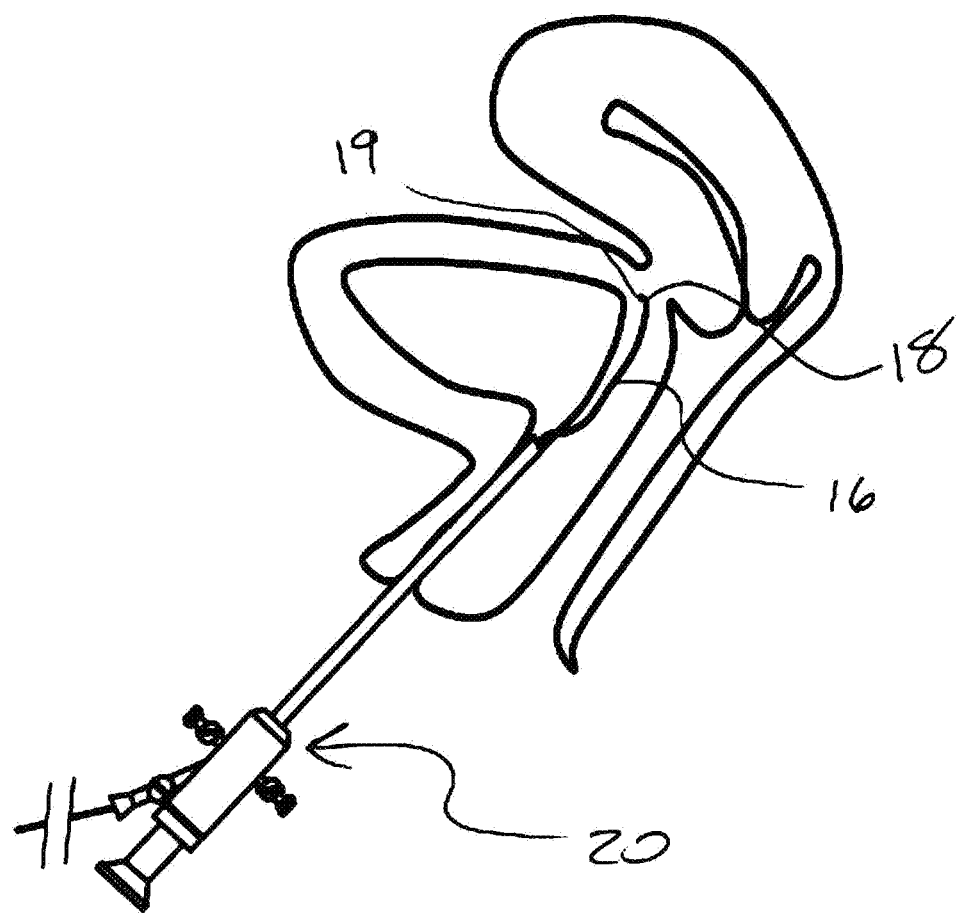
FIG. 11 is a diagram of an embodiment of a visualization scope of the invention being used in an embodiment of a method of the invention.

The guide wire 16 may be flexible and steerable, with a pre-formed curve 18 at the distal end. The guide wire may be initially placed transurethrally with the aid of the cystoscope 20, as shown in FIG. 11. Initially the cystoscope 20 is placed in the urethra to a site where entry of the guide wire 16 is desired to be placed submucosally. The guide wire may have a sharpened tip 19 to aid in penetrating the surface and advancing submucosally. A cautery device or other tissue penetrator may also be used to initially access the submucosal space. Imaging may also be used to facilitate navigation and placement, such as fluoroscopy or ultrasound.

Figure 12:
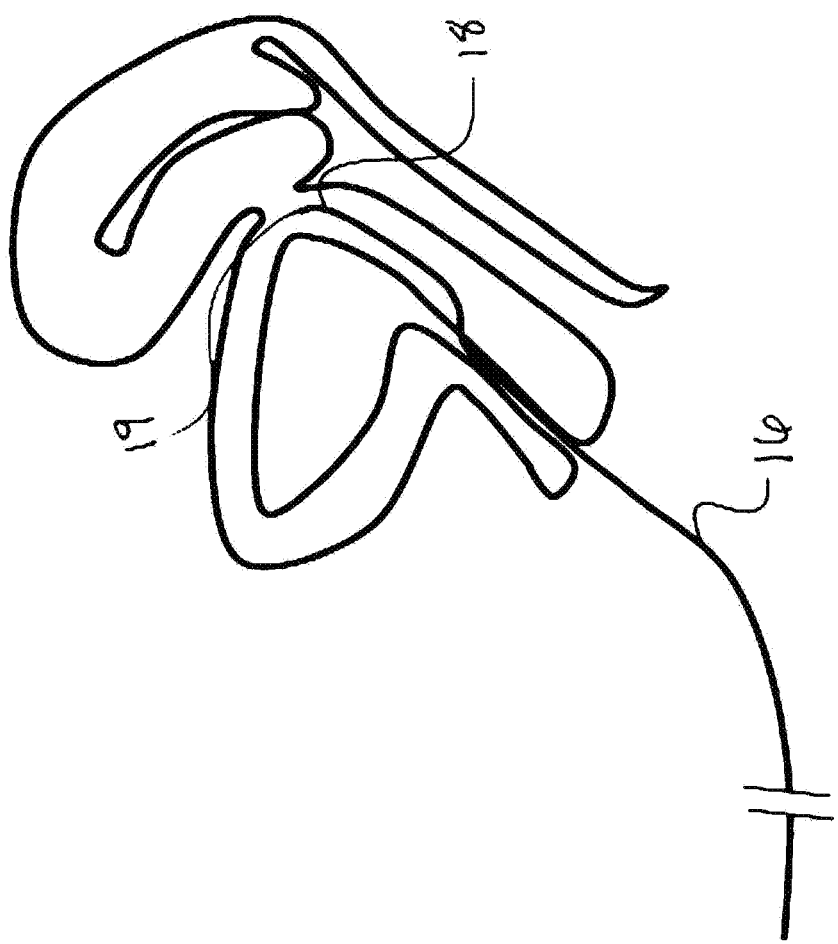
FIG. 12 is a diagram of an embodiment of a guidewire of the invention placed in a female urogenital region by an embodiment of a method of the invention.
Figure 13:
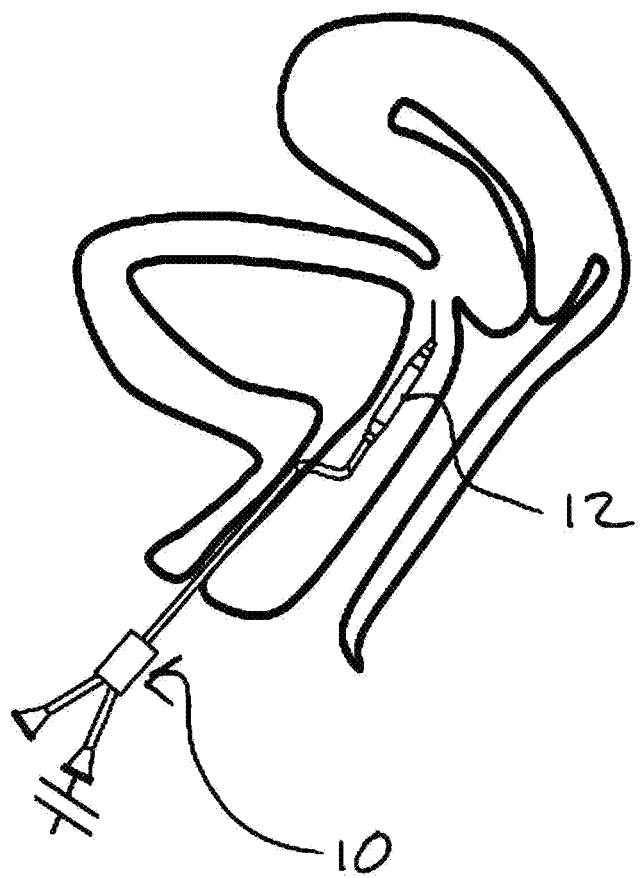
FIG. 13 is a diagram of an embodiment of a catheter of the invention being used in an embodiment of a method of the invention.

Once the guide wire 16 is positioned, the cystoscope 20 may be removed, or may be left in place and the balloon catheter 10 advanced over the guide wire 16 and within the working channel 28. FIG. 12 shows the cystoscope 20 removed. FIG. 13 shows the balloon catheter 10 advanced over the guide wire to the target site for dilation. Positioning of the balloon 12 may be aided with markers (not shown) on the guide wire that at a known distance from the tip, coupled with a known length of balloon catheter, resulting in the tip of the balloon catheter being positioned a known distance from the guide wire. FIG. 4 shows the balloon in an inflated condition.

Figure 5:
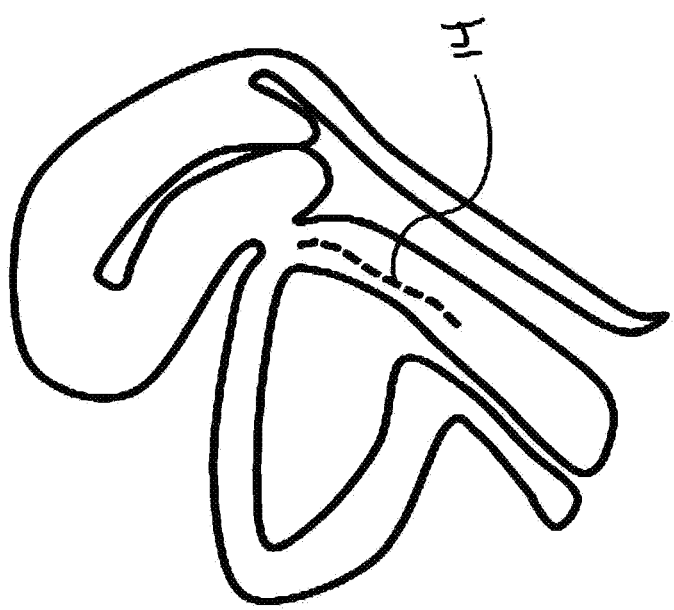
FIG. 5 is a diagram of a dissection layer formed by an embodiment of a method of the invention.

FIG. 5 is a side view showing the dissection plane 14 within the tissue between the bladder trigone region and the vagina. And, as mentioned above, FIG. 6 shows the areas in an exemplary treatment with three dissection regions 14 following three balloon placements and inflations.

As with other embodiments of the invention, similar techniques could be performed via a trans-vaginal approach, where the balloon catheter is placed into the same region, but via the superior portion of the vagina.

Figure 15:
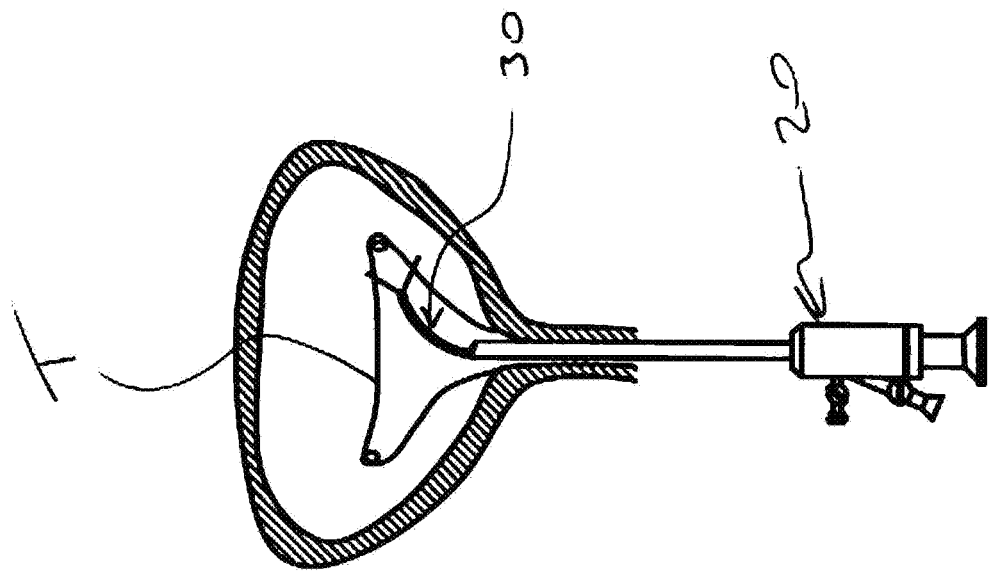
FIGS. 14-15 depict an embodiment of a cutting device of the invention being used in an embodiment of a method of the invention.
Figure 14:
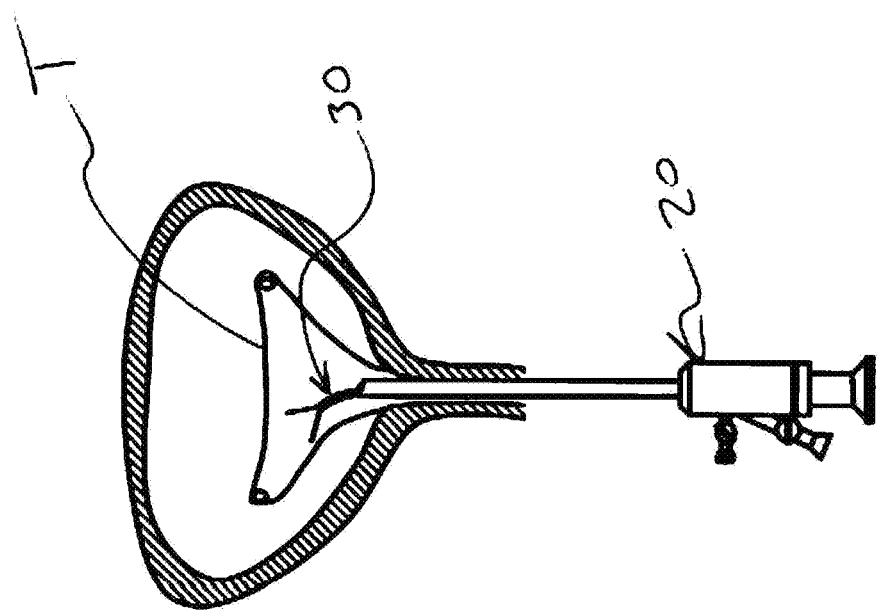

FIGS. 14 and 15 illustrate an alternative embodiment of the invention. Here, a cutting device 30 is positioned in the submucosal space of the bladder trigone T. Cutting device 30 may be positioned in similar locations as described above in connection with the balloon embodiments.

Cutting device 30 may be one of the cutting devices used in other minimally invasive surgical procedures, such as those used through working channels of cyctoscopes for other urological or gynecological procedures, or other scope devices used in other human minimally invasive surgical procedures. Such devices may be steerable and/or deflectable. Furthermore they may also incorporate cautery or other energy combined with cutting to achieve cutting while minimizing bleeding.

The cutting device 30 may be positioned with the aid of a cystoscope 20, an exemplary version of which was illustrated in FIGS. 7 and 8, via a working channel 28. Cutting device 30 may be further positioned with the aid of a guide wire 16, similar to that described in connection with the balloon catheter embodiments. The cutting device 30 may also be advanced in a tissue plane that has a natural "separability", such as between the bladder mucosa and submucosa, or between the bladder trigone submucosa and the vaginal submucosa.

Figure 16:
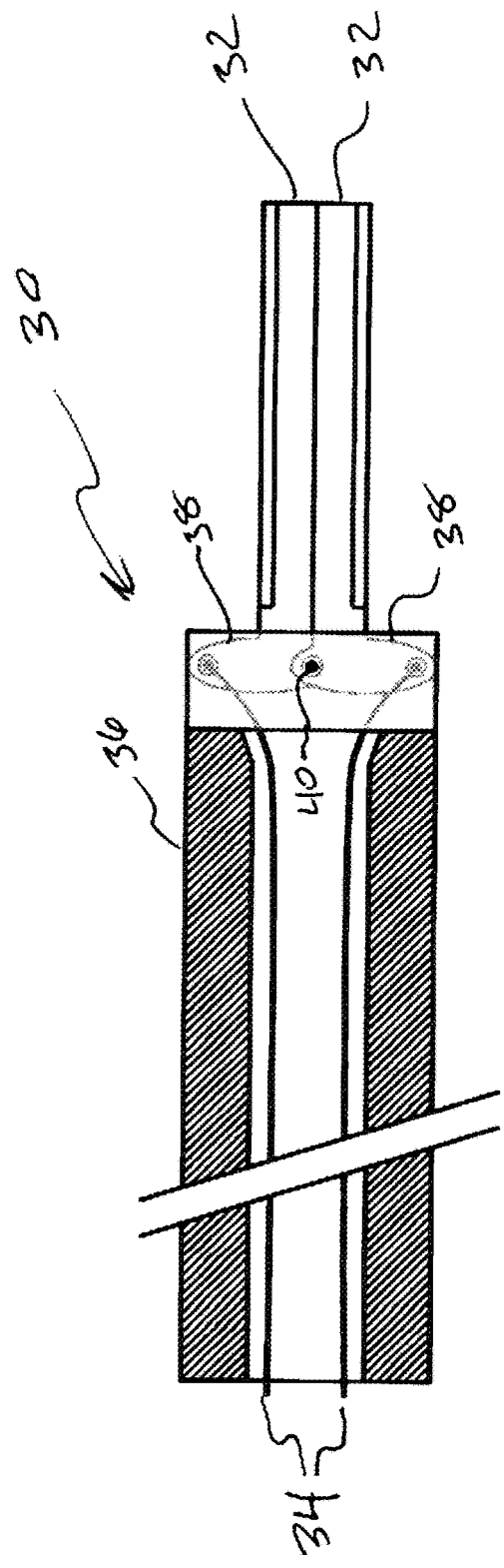
FIGS. 16-17 are elevations of an embodiment of a cutting device of the invention with cutaways showing internal components.
Figure 17:
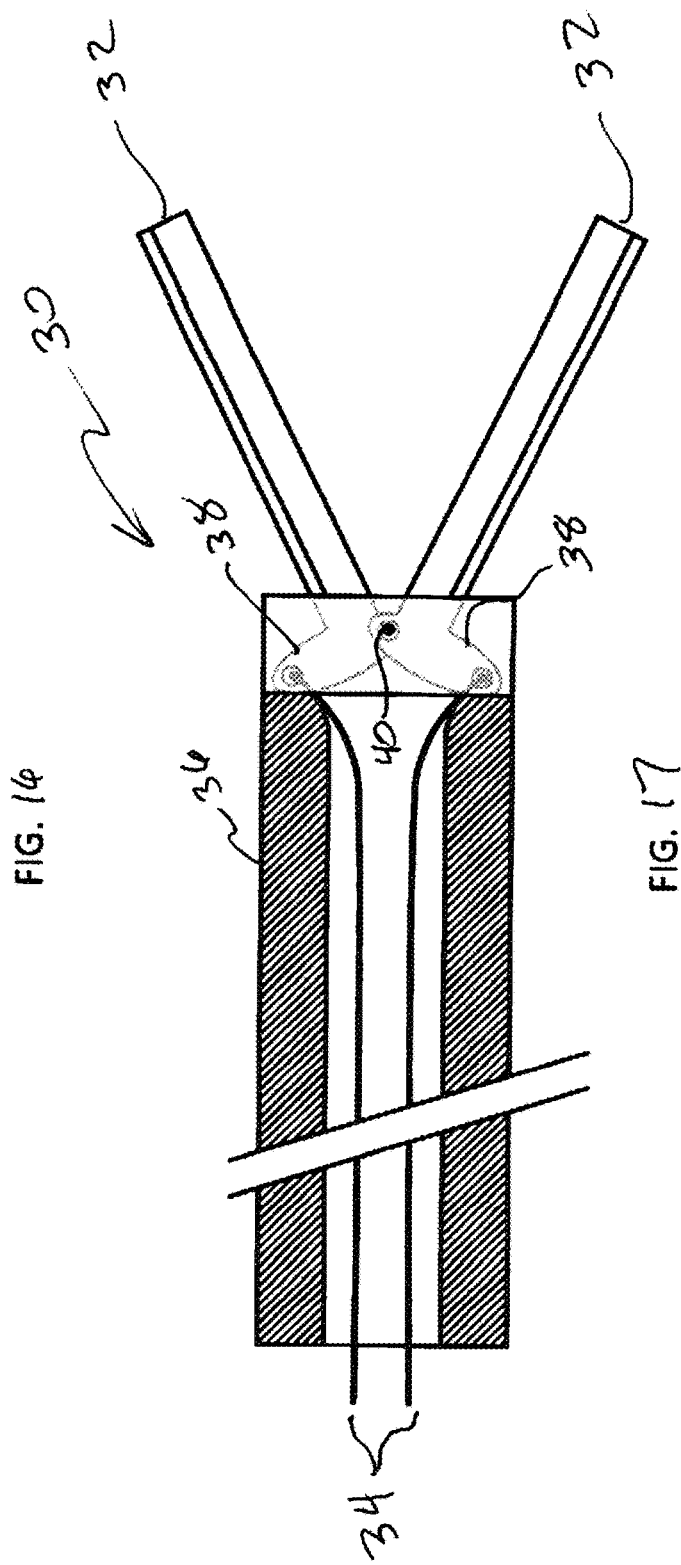

FIGS. 16 and 17 illustrate a novel and particularly useful embodiment of a cutting device 30 for making submucosal dissection planes. Cutting device 30 includes 2 laterally extendable blades 32, with cutting surfaces on their outer (lateral) aspects. When the cutting device is placed in a target position, it is initially "closed", as shown in FIG. 16. Then the device is "opened", by relative movement between the activation tethers 34 and the body, creating a dissection plane wider than the device. The activation tethers pull on the lever arms 38 of the cutting blades, and the cutting blades rotate outward about a pivot 40. The cutting device may be further advanced to make a more elongate dissection plane. The cutting device may be repositioned to make multiple laterally displaced cutting planes 14, as shown in FIG. 6. Such dissection planes 14 may ultimately be conjoined to form one relatively large dissection plane in the submucosal region of the bladder trigone.

Figure 20:
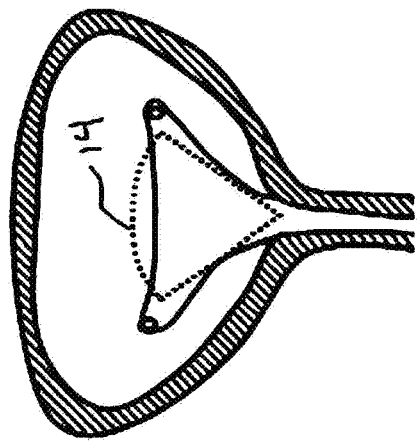
FIGS. 18-20 depict an embodiment of a cutting device of the invention being used in an embodiment of a method of the invention.
Figure 19:
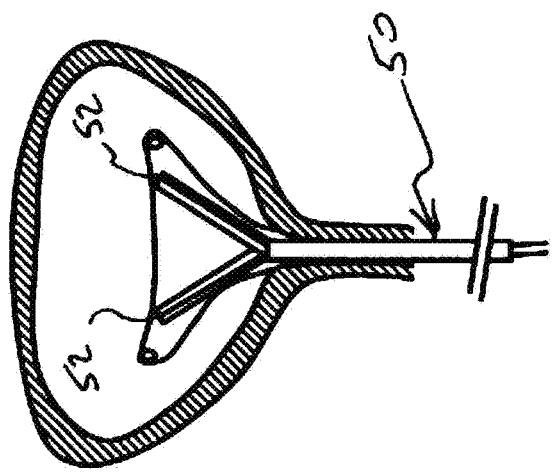
Figure 18:
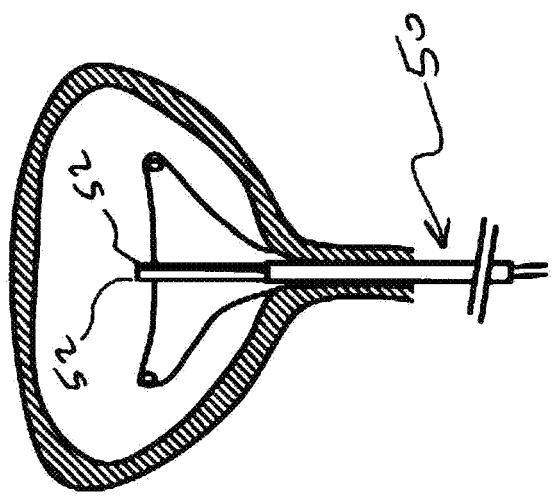
Figure 21:
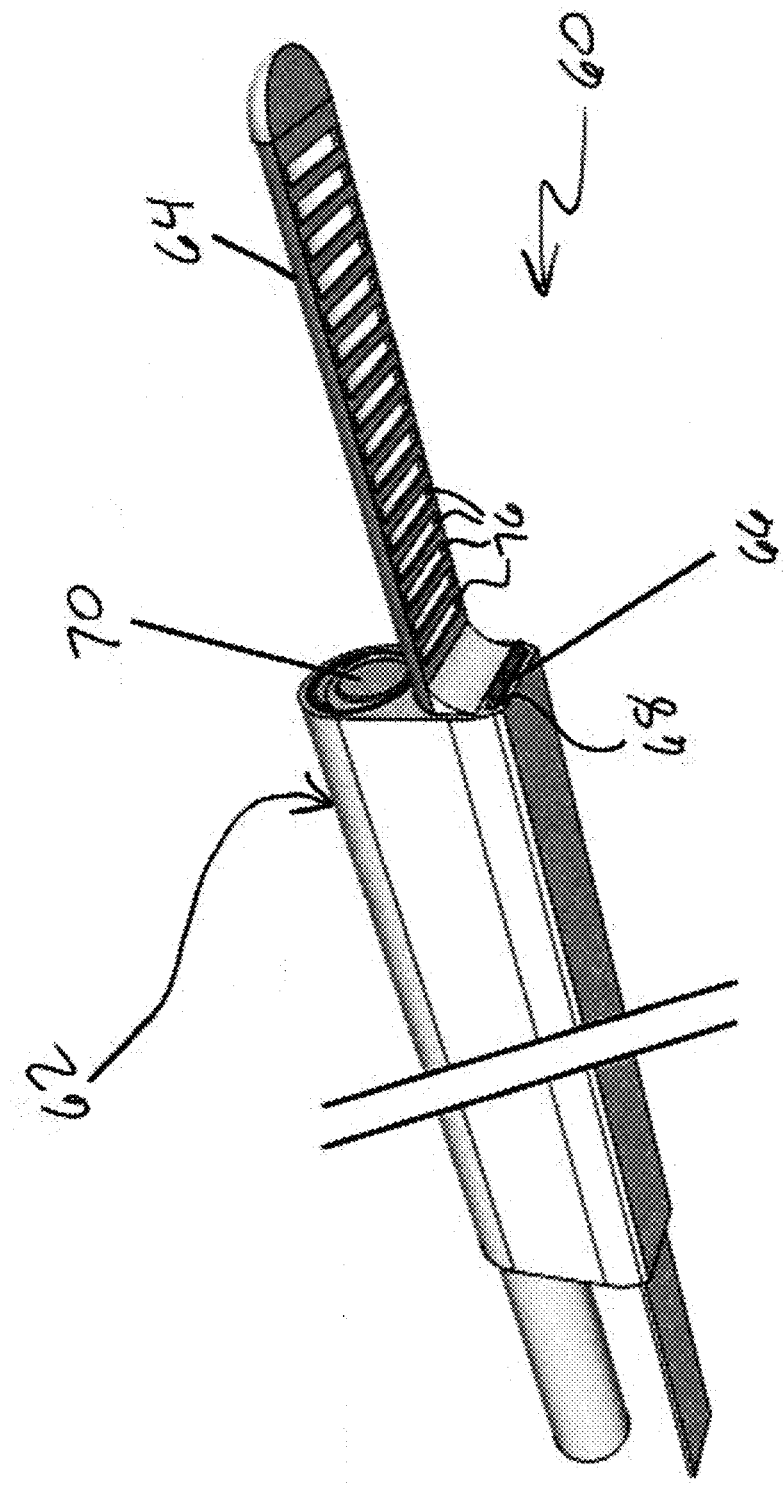
FIG. 21 is a perspective view of an embodiment of a cutting device of the invention.

FIGS. 18-19 show another embodiment 50 of a cutting device. Here, the blades 52 may be relatively long, and as such may create a larger dissection plane 14 in the submucosal surface when the blades are opened laterally, as shown in FIGS. 18-20.

As with the balloon embodiments, these cutting device embodiments may also be used from the vaginal side of the bladder trigone to create one or more submucosal dissection planes.

FIGS. 21-25 illustrate yet another alternative embodiment 60 for a cutting tool. Here cutting tool 60 may include a positioning guide 62. Positioning guide 62 may include a suction paddle 64 for engagement with the bladder mucosa, and a cutting blade 66 (shown retracted) within a cutting blade lumen 68, and a visualization device 70 such as an endoscope.

In operation, the positioning guide 62 is placed into the bladder transurethrally to a site of interest, such as adjacent the trigone region. If a dissection plane is to be made, the suction paddle 64 is placed against the bladder mucosa in the region to be submucosally dissected. Note that the endoscope 70 may be movable longitudinally within the scope channel 72 to help with precise placement of the distal tip of the suction paddle 64, as seen in FIG. 26. Advancing the endoscope 70 to near the tip can be particularly advantageous to accurately position the tip relative to the ureteral orifices in order to avoid damage to them.

Once in a desired location, the suction paddle 64 is activated by applying suction to the suction lumen 74 (FIG. 24). Valves (not shown) operative with the lumen 74 may be incorporated. Apertures 76 in the tissue face of the suction paddle 64 then securely engage the mucosal tissue. The blade is then advanced, as seen in FIG. 28. Because the cutting blade lumen is parallel to but offset from the tissue face, as shown in FIG. P3, the cutting blade cuts a dissection plane at a predetermined depth submucosally. A handle mechanism (not shown) may be incorporated to manage and control the positions of the proximal ends of the cutting blade and/or the endoscope.

The positioning guide 62 can be placed in multiple locations by repeatedly removing suction, manipulating the guide, re-applying suction, and re-advancing the blade. In this manner, multiple submucosal dissection planes can be generated in the bladder trigone area.

As with other embodiments above, the cutting blade 66 may incorporate cautery, such as monopolar RF applied to the blade, or bipolar RF energy applied from the blade to the suction head. In such a case, portions of the cutting blade and suction head are appropriately conductive, and adjoining surfaces are appropriately electrically insulated.

Also, as with other embodiments above, the positioning guide embodiments may be utilized via a trans-vaginal approach.

In yet a further embodiment, the positioning guide 62 described above, with the suction paddle 64, may be used with other cutting mechanisms that are placed submucosally via the cutting channel. An appropriately sized cutting channel is incorporated, depending on the size and shape of the cutting device to be used.

Figure 29:
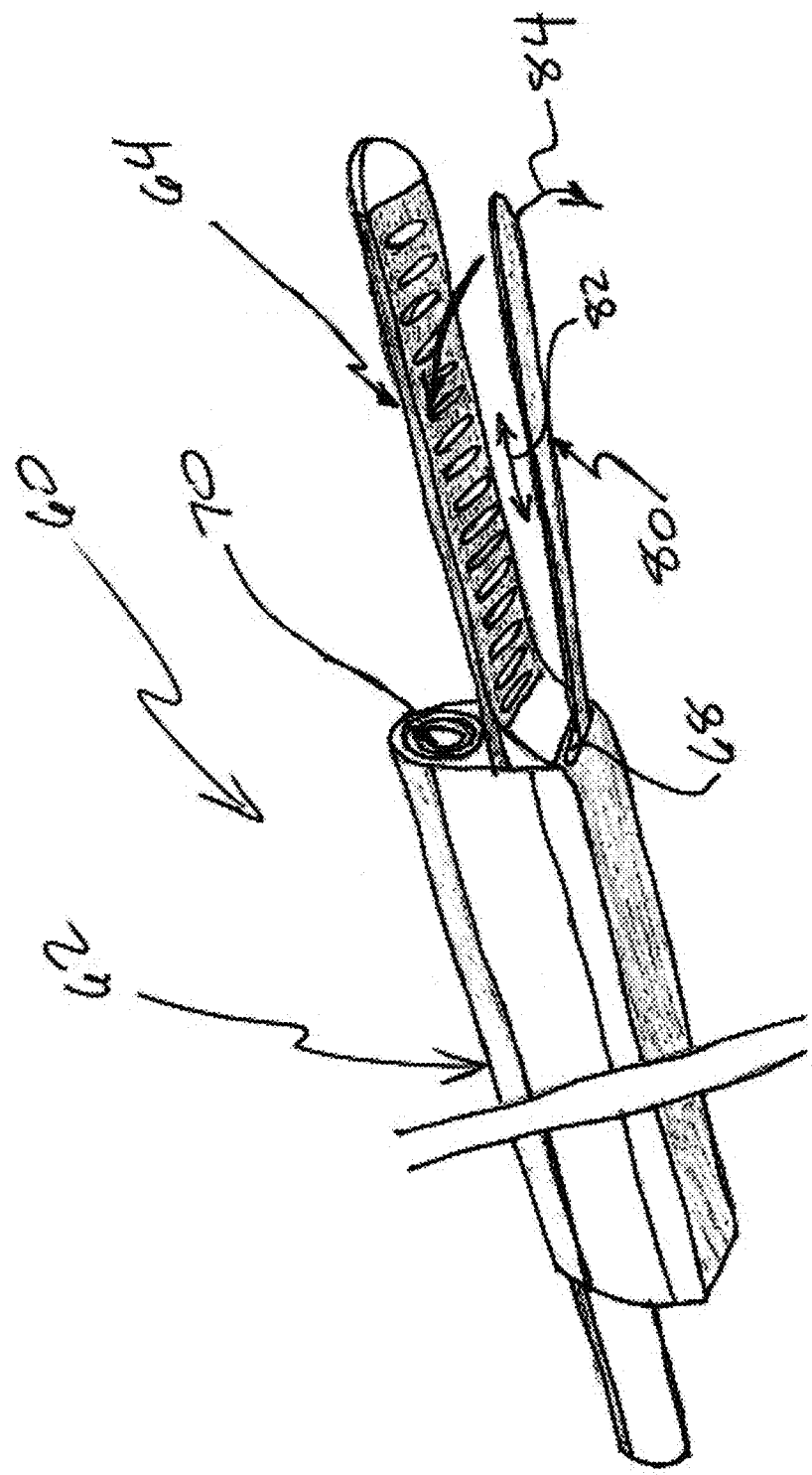

For example, FIG. 29 shows the cutting device 60 employing a translatable cutting mechanism 80. In addition to being able to be advanced and retracted longitudinally, as shown by arrow 82, the cutting mechanism 80 as able to be translated from side to side as shown in arrow 84. In order to maximize translation, a pivot point (not shown) is located as near the distal opening of the lumen 68 when the mechanism 80 is advanced longitudinally to its distal extent. The sides of the lumen 68 may act as translation limits. In this way, the desired degree of translation may be controlled by the amount the mechanism 80 is advanced distally. Retracting the mechanism 80 proximally reduces the degree to which the mechanism 80 may be translated side-to-side.

It is understood that mechanism 80 may comprise a blade or needle and may be energized for ablation, to form a lesion, or cauterization. If a needle is used as the mechanism 80, the translation feature is used prior to advancing the needle out of the lumen 68, and is thus used to control the angular direction the needle travels out of the lumen. In this way, several injection lines may be effected without repositioning the positioning guide 62.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof. For example, one alternative to the methods of the invention may include trans-urethral trigonal resection—whether by mechanical or energy delivery (including cryo) means. Resection may involve removal or destruction of a layer of desired thickness (ranging from the 1 mm mucosal thickness to the 5-6 mm complete bladder wall thickness) which would include nerves and nerve endings involved in OAB. As an additional example, the devices described above may be modified (e.g. by making longer and/or flexible) for use in the male anatomy.

What is claimed is:

1. A method of creating at least one dissection plane within a wall of a bladder trigone of a patient, the method comprising:
   advancing a visualization scope through a urethra of the patient until a distal end portion of the scope is positioned in the patient's bladder, the scope including a working channel therethrough;
   advancing a guide wire through the working channel, until a tissue penetrating distal tip of the guide wire is advanced out an open distal end of the working channel and penetrates a wall of the bladder;
   advancing the distal tip of the guidewire submucosally through the bladder wall until the distal tip of the guidewire is positioned within tissue of the bladder trigone;
   advancing a balloon dilation catheter over the guidewire until a balloon carried on a distal end portion of the balloon dilation catheter is positioned proximate the distal tip of the guidewire within the bladder trigone tissue;
   and
   while the balloon is within the wall of the bladder trigone, inflating said balloon to form a first dissection plane between separated layers of tissue within the bladder trigone.

2. The method of claim 1, further comprising placing a Fogarty balloon in the bladder to keep dissected tissues adjacent the first dissection plane in approximation.

3. The method of claim 1, wherein a distal end portion of the guide wire has a pre-formed curve to facilitate positioning of the balloon at a desired depth in the bladder trigone tissue.

4. The method of claim 1, wherein the balloon is inflated at a first location in the bladder trigone, the method further comprising
   after said inflating, deflating the balloon;
   relocating the balloon dilation catheter so that the balloon is positioned at a second location in the bladder trigone; and
   re-inflating the balloon to (i) form a second dissection plane between separated layers of tissue within the bladder trigone or (ii) extend the first dissection plane between the separated layers of tissue within the bladder trigone.

5. The method of claim 1, wherein said advancing the visualization scope through a urethra of the patient comprises positioning the distal end portion of the scope in the patient's bladder so that the open distal end of the working channel is adjacent a targeted entry site on the bladder wall spaced apart from the trigone through which the distal tip of the guidewire is intended to penetrate.

6. The method of claim 1, wherein the balloon dilation catheter is positioned within the bladder trigone tissue based on markers provided on the guidewire.

7. A method of creating at least one dissection plane within a wall of a bladder trigone, the method comprising:
   placing a cutting tool at the bladder trigone via a urethra, said cutting tool including a suction paddle and a planar blade spaced apart from and generally parallel to a surface of said suction paddle;
   applying suction to said suction paddle to engage tissue of the bladder trigone; and,
   forming a dissection plane between separated layers of tissue within the wall of the bladder trigone by advancing said blade through said engaged tissue.

8. The method of claim 7, wherein the blade is advanced generally parallel to the suction paddle surface.

9. The method of claim 7, further comprising conducting radiofrequency (RF) energy between the blade and the suction head.

10. The method of claim 7, wherein the blade is first advanced along a longitudinal axis of the cutting tool, and then the blade is advanced in a lateral direction relative to the longitudinal axis.

11. The method of claim 7, wherein placing a cutting tool at the bladder trigone via a urethra comprises places the cutting tool at a first location on the bladder trigone, the method further comprising repositioning the cutting tool at a different location on the bladder trigone and advancing the blade to either
   form an additional dissection plane between separated layers of tissue, or
   extend the dissection plane between the separated layers of tissue.

12. The method of claim 7, wherein the cutting tool includes an endoscope.

13. The method of claim 10, wherein said advancing said blade in a lateral direction comprises translating the blade side-to-side about a pivot point.

14. The method of claim 13, wherein said blade is advanced out of a lumen of the cutting instrument into the bladder trigone such that the pivot point is located within a distal portion of the lumen to limit the lateral translation of the blade.

15. A method of treating over active bladder, the method comprising:
   advancing a device through a urethra and into tissue below a surface of a trigone region of a bladder such that a portion of the device including a cutting blade extends into tissue between the surface of the trigone region of the bladder and a vaginal surface; and
   creating a dissection plane between separated layers of tissue within the tissue between the surface of the trigone region of the bladder and the vaginal surface by advancing the cutting blade within the bladder trigone tissue to disrupt nerves associated with over active bladder.

16. The method of claim 15, wherein said blade comprises a first blade of the cutting device, the cutting device comprising a second blade, the method further comprising using an actuator coupled to said first and second blades to rotate each of said first and second blades back and forth laterally relative to a longitudinal axis of the cutting device in the tissue between the surface of the trigone region of the bladder and a vaginal surface.

17. The method of claim 15, wherein said cutting device is advanced through the urethra by advancing the device through a working channel of a visualization scope positioned in the urethra.

18. The method of claim 15, wherein said cutting device includes a positioning guide configured to engage tissue at the surface of the trigone region of the bladder.

* * * * *